United States Patent [19]

Marler

[11] Patent Number: 5,329,059
[45] Date of Patent: Jul. 12, 1994

[54] ALKYLAROMATIC DISPROPORTIONATION

[75] Inventor: David O. Marler, Deptford, N.J.

[73] Assignee: Mobil Oil Corp., Fairfax, Va.

[21] Appl. No.: 86,256

[22] Filed: Jul. 6, 1993

[51] Int. Cl.$^5$ ............................................. C07C 5/52
[52] U.S. Cl. ............................................. 585/475; 585/471
[58] Field of Search .................................. 585/475, 471

[56] References Cited

U.S. PATENT DOCUMENTS

| | | | |
|---|---|---|---|
| 3,126,422 | 3/1964 | Planchard | 260/671 |
| 3,413,374 | 11/1968 | Sato et al. | 260/672 |
| 3,598,878 | 8/1971 | Kovach et al. | 260/672 |
| 3,598,879 | 8/1971 | Kmecak et al. | 260/672 |
| 3,607,961 | 9/1971 | Kovach et al. | 260/672 R |
| 4,117,026 | 9/1978 | Haag et al. | 260/671 R |
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 4,962,257 | 10/1990 | Absil et al. | 585/475 |
| 4,982,040 | 1/1991 | Angevine et al. | 585/475 |
| 5,030,787 | 7/1991 | Absil et al. | 585/475 |
| 5,043,501 | 8/1991 | Del Rossi et al. | 585/323 |
| 5,210,356 | 5/1993 | Shamshouni et al. | 585/475 |
| 5,236,575 | 8/1993 | Bennett et al. | 423/718 |
| 5,243,117 | 9/1993 | Chang et al. | 585/475 |

FOREIGN PATENT DOCUMENTS 0293032 11/1988 European Pat. Off.

Primary Examiner—Anthony McFarlane
Attorney, Agent, or Firm—Alexander J. McKillop; Malcolm D. Keen; Dennis P. Santini

[57] ABSTRACT

A process is provided for disproportionation of an alkylaromatic compound, alkyl being from 1 to about 6 carbon atoms, e.g., toluene and methylnaphthalene, comprising contacting said compound with catalyst comprising an active form of synthetic porous crystalline MCM-49.

19 Claims, No Drawings

ALKYLAROMATIC DISPROPORTIONATION

BACKGROUND OF THE INVENTION

This invention relates to a process for the catalytic disproportionation of alkylaromatic compounds, e.g., toluene, methylnaphthalene, and the like, over catalyst comprising an active form of synthetic porous crystalline material having the structure of MCM-49.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of large dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g., $AlO_4$, in which the tetrahedra are cross-linked by the sharing of oxygen atoms whereby the ratio of the total Group IIIB element, e.g., aluminum, and silicon atoms to oxygen atoms is 1:2. The electrovalence of the tetrahedra containing the Group IIIB element, e.g., aluminum, is balanced by the inclusion in the crystal of a cation, e.g., an alkali metal or an alkaline earth metal cation. This can be expressed wherein the ratio of the Group IIIB element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842).

The $SiO_2/Al_2O_3$ ratio of a given zeolite is often variable. For example, zeolite X can be synthesized with $SiO_2/Al_2O_3$ ratios of from 2 to 3; zeolite Y, from 3 to 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. No. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

U.S. Pat. Nos. 3,126,422; 3,413,374; 3,598,878; 3,598,879; and, 3,607,961 describe the vapor-phase disproportionation of toluene over various catalysts. U.S. Pat. No. 4,117,026 discloses disproportionation of toluene over a catalyst comprising a zeolite having a silica/alumina mole ratio of at least 12, a Constraint Index of 1 to 12 and a specified sorption capacity for xylenes. U.S. Pat. No. 5,030,787 teaches toluene disproportionation with C9+ co-feed.

U.S. Pat. No. 4,962,257 describes disproportionation of toluene over catalyst comprising, for example, MCM-22 or PSH-3. U.S. Pat. No. 4,982,040 describes disproportionation of methylnaphthalenes, such as 2-methylnaphthalene, to a product comprising naphthalene and a mixture of dimethylnapthalene isomers over catalyst comprising, for example, PSH-3 or MCM-22. U.S. Pat. No. 5,043,501 teaches use of zeolites such as, for example, MCM-22 and PSH-3 as catalyst for producing 2,6-dimethylnapthalene by alkylation of alkylaromatic, e.g., toluene, with a C5 olefin alkylating agent, e.g., 1-pentene, followed by dehydrocyclization of the resulting alkylate with a dehydrocyclization catalyst.

U.S. Pat. No. 4,439,409 describes PSH-3 and its synthesis from a reaction mixture containing hexamethyleneimine, an organic compound which acts as directing agent for synthesis of the presently used MCM-49. A composition of matter appearing to be identical to the PSH-3 of U.S. Pat. No. 4,439,409, but with additional structural components, is taught in European Patent Application 293,032. Hexamethyleneimine is also used for synthesis of MCM-22 in U.S. Pat. No. 4,954,325; MCM-35 in U.S. Pat. No. 4,981,663; and a ZSM-12 material in U.S. Pat. No. 5,021,141. A composition of matter referred to as zeolite SSZ-25 is taught in U.S. Pat. No. 4,826,667 and European Patent Application 231,860, said zeolite being synthesized from a reaction mixture containing an adamantane quaternary ammonium ion. MCM-49 is described in U.S. patent application Ser. No. 07/802,938, incorporated entirely herein by reference.

SUMMARY OF THE INVENTION

The present invention resides in a process for the disproportionation of alkylaromatic compounds, e.g., toluene, which comprises contacting feedstock comprising said alkylaromatic compound with a conversion catalyst comprising an active form of synthetic porous crystalline MCM-49.

MCM-49 is characterized as-synthesized by an X-ray diffraction pattern including interplanar d-spacings at 13.15±0.26, 12.49±0.24, 11.19±0.22, 6.43±0.12, 4.98±0.10, 4.69±0.09, 3.44±0.07, and 3.24±0.06 Angstroms. The d-spacing maximum at 13.15±0.26 Angstroms is observed as a shoulder of the intense peak at 12.49±0.24 Angstroms.

As is demonstrated hereinafter, MCM-49 has exceptionally high activity for the present process, while demonstrating like selectivity when compared to MCM-22.

DESCRIPTION OF THE SPECIFIC EMBODIMENTS

The feedstock employed in the present process is preferably dried to minimize water entering the reaction zone. Known methods for drying such feedstocks, e.g., toluene; are numerous, including percolation through silica gel, activated alumina, molecular sieves or other suitable substances or the use of liquid charge dryers.

In general, the feedstocks comprise any alkylaromatic compound, alkyl having from 1 to about 6 carbon atoms. Non-limiting examples of such compounds for use herein include toluene, methylnaphthalene, cumene, ethylbenzene, butylbenzene, ethylnaphthalene, isopropylnaphthalene, methylbiphenyl and mixtures thereof.

When toluene is to be disproportionated in this process, products comprise benzene and xylene isomers. Methylnaphthalene disproportionates hereby to product comprising naphthalene and dimethylnaphthalene isomers. Of the dimethylnaphthalene isomers, 2,6-dimethylnaphthalene is a key intermediate in the production of 2,6-napthalenedicarboxylic acid, a valuable monomer for specialty polyester manufacture.

When toluene is the alkylaromatic to be disproportionated by the present process, the feedstock may contain other aromatic hydrocarbons, including $C_9+$ aromatics. When present, the $C_9+$ aromatics may constitute up to 70 wt. % of the total feedstock.

In general, the process of the invention can be conducted over a wide range of conversion conditions, including a temperature of from about 175° C. to about 675° C., a pressure of from about atmospheric to about 2,000 psig, a weight hourly space velocity (WHSV) of from about 0.1 $hr^{-1}$ to about 500 $hr^{-1}$, and a hydrogen/hydrocarbon ($H_2$/HC) mole ratio of from 0 (no added hydrogen) to about 10. When the feedstock comprises toluene to be disproportionated, the temperature is from about 250° C. to about 595° C., preferably from about 315° C. to about 595° C.; the pressure is from about atmospheric to about 1,000 psig, preferably from about 200 psig to about 1,000 psig; the WHSV is from about 0.1 $hr^{-1}$ to about 30 $hr^{-1}$, preferably from about 0.5 $hr^{-1}$ to about 15 $hr^{-1}$; and the $H_2$/HC mole ratio is from 0 to about 10, preferably from about 0.25 to about 5. When the feedstock comprises alkylnaphthalene, e.g., methylnaphthalene, to be disproportionated, the temperature is from about 250° C. to about 675° C., preferably from about 350° C. to about 575° C.; the pressure is from about atmospheric to about 3000 psig, preferably from about 200 psig to about 1,000 psig; the WHSV is from about 0.1 $hr^{-1}$ to about 500 $hr^{-1}$, preferably from about 0.5 $hr^{-1}$ to about 100 $hr^{-1}$; and the $H_2$/HC mole ratio is from 0 to about 10, preferably from about 0.25 to about 5.

The crystalline material MCM-49 for use as catalyst component in this invention is described in U.S. patent application Ser. No. 07/802,938, entirely incorporated herein by reference, and has a composition involving the molar relationship:

$$X_2O_3:(n)YO_2,$$

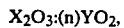

wherein X is a trivalent element, such as aluminum, boron, iron and/or gallium, preferably aluminum; Y is a tetravalent element such as silicon, titanium, and/or germanium, preferably silicon; and n is less than about 35, e.g. from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

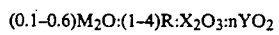

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline material for use in the invention is thermally stable and in the calcined form exhibits high surface area (greater than 400 m²/gm) and unusually large sorption capacity when compared to previously described materials such as calcined PSH-3 (U.S. Pat. No. 4,439,409) and SSZ-25 (U.S. Pat. No. 4,826,667) having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g., ammonium, ions, and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB, VIB and VIII of the Periodic Table of Elements.

In the as-synthesized form, the crystalline MCM-49 material for use in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

The X-ray diffraction peak at 13.15±0.26 Angstrom Units (A) is usually not fully resolved for MCM-49 from the intense peak at 12.49±0.24, and is observed as a shoulder of this intense peak. For this reason, the precise intensity and position of the 13.15±0.26 Angstroms peak are difficult to determine within the stated range.

In its calcined form, the crystalline MCM-49 material for use in the invention is a single crystal phase with little or no detectable impurity crystal phases having an X-ray diffraction pattern which is not easily distinguished from that of MCM-22, but is readily distinguishable from the patterns of other known crystalline materials. The X-ray diffraction pattern of the calcined form of MCM-49 includes the lines listed in Table II below:

TABLE II

| Interplanar d-Spacing (A) | Relative Intensity, I/Io × 100 |
|---|---|
| 12.41 ± 0.24 | vs |
| 11.10 ± 0.22 | s |
| 8.89 ± 0.17 | m-s |
| 6.89 ± 0.13 | w |

TABLE II-continued

| Interplanar d-Spacing (A) | Relative Intensity, I/Io × 100 |
|---|---|
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60-100), s=strong (40-60), m=medium (20-40) and w=weak (0-20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 with similar materials, e.g., MCM-22 and PSH-3.

The significance of differences in the X-ray diffraction patterns of these materials can be explained from a knowledge of the structures of the materials. MCM-22 and PSH-3 are members of an unusual family of materials, because upon calcination, there are changes in the X-ray diffraction pattern that can be explained by a significant change in one axial dimension. This is indicative of a profound change in the bonding within the materials and not a simple loss of the organic material. The precursor members of this family can be clearly distinguished by X-ray diffraction from the calcined members. An examination of the X-ray diffraction patterns of both precursor and calcined forms shows a number of reflections with very similar position and intensity, while other peaks are different. Some of these differences are directly related to the changes in the axial dimension and bonding.

The present as-synthesized MCM-49 has an axial dimension similar to those of the calcined members of the family and, hence, there are similarities in their X-ray diffraction patterns. Nevertheless, the MCM-49 axial dimension is different from that observed in the calcined materials. For example, the changes in axial dimensions in MCM-22 can be determined from the positions of peaks particularly sensitive to these changes. Two such peaks occur at ~13.5 Angstroms and ~6.75 Angstroms in precursor MCM-22, at ~12.8 Angstroms and ~6.4 Angstroms in as-synthesized MCM-49, and at ~12.6 Angstroms and ~6.30 Angstroms in the calcined MCM-22. Unfortunately, the ~12.8 Angstroms peak in MCM-49 is very close to the intense ~12.4 Angstroms peak observed for all three materials, and is frequently not fully separated from it. Likewise, the ~12.6 Angstroms peak of the calcined MCM-22 material is usually only visible as a shoulder on the intense ~12.4 Angstroms peak. Because the ~6.4 Angstroms peak is unobscured in MCM-49, it was chosen as a better means of distinguishing MCM-49 from the calcined forms of MCM-22 and PSH-3 rather than the much stronger ~12.8 Angstroms peak. Table I lists all diffraction peaks characteristic of MCM-49.

MCM-49 can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, directing agent (R), and water, said reaction mixture having a composition, in terms of mole ratios of oxides, within the following ranges:

| Reactants | Useful | Preferred |
|---|---|---|
| $YO_2/X_2O_3$ | 12 to <35 | 18 to 31 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/X_2O_3$ molar ratio thereof is less than about 35. For example, if aluminum oxide and gallium oxide components are used in the reaction mixture, at least one of the $YO_2/Al_2O_3$ and $YO_2/Ga_2O_3$ molar ratios must be less than about 35. If only aluminum oxide has been added to the reaction mixture as a source of X, the $YO_2/Al_2O_3$ ratio must be less than about 35.

In the above synthesis method, the source of $YO_2$ must be comprised predominately of solid $YO_2$, for example at least about 30 wt. % solid $YO_2$. When $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the $YO_2$, e.g. silica, source contains at least about 30 wt. % solid $YO_2$, e.g. silica, and more preferably at least about 40 wt. % solid $YO_2$, e.g. silica.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexlamine, cycloheptylamine, hexamethyleneimine, heptamethyleneimine, homopiperazine, and combinations thereof.

Crystallization of MCM-49 crystalline material can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of MCM-49 crystalline material will vary with the nature of the reaction mixture employed and the crystallization conditions.

Synthesis of MCM-49 may be facilitated by the presence of at least 0.01 percent, preferably 0.10 percent and still more preferably 1 percent, seed crystals (based on total weight) of crystalline product. Useful seed crystals include those having the structure of MCM-49.

The crystals prepared as above for use herein can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

Zeolite MCM-49, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the disproportionation process of this invention, the zeolite MCM-49 crystals should be dehydrated, at least partially. This can be done by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

It may be desired to incorporate the MCM-49 with another material resistant to the temperatures and other conditions employed in organic conversion processes. Such materials include active and inactive materials and synthetic or naturally occurring zeolites as well as inorganic materials such as clays, silica and/or metal oxides such as, for example, alumina, titania or zirconia. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the MCM-49 crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the MCM-49 crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of zeolite MCM-49 may be increased by combining the as-synthesized MCM-49 with an alumina binder, converting the alumina-bound MCM-49 to the hydrogen form, (i.e., HMCM-49) and steaming the alumina-bound HMCM-49 composition under conditions sufficient to increase the stability of the catalyst. U.S. Pat. Nos. 4,663,492; 4,594,146; 4,522,929; and 4,429,176, the entire disclosures of which are incorporated herein by reference describe conditions for the steam stabilization of zeolite catalysts which can be utilized to steam-stabilize alumina-bound HMCM-49. The steam stabilization conditions include contacting the alumina bound HMCM-49 with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

catalyst, while increasing further with MCM-49 catalyst, all the while maintaining selectivity.

TABLE III

| | TOLUENE DISPROPORTIONATION 5 WHSV, 0 psig | | | | | | | | |
|---|---|---|---|---|---|---|---|---|---|
| | MCM-22 Exchanged Once | | | MCM-22 Exchanged Twice | | | MCM-49 Exchanged Once | | |
| Temperature, °C. | 260 | 315 | 371 | 260 | 315 | 371 | 260 | 315 | 371 |
| Toluene Conversion, wt. % | 8.6 | 11.1 | 11.9 | 9.8 | 10.5 | 10.7 | 9.3 | 10.4 | 14.1 |
| Selectivities, wt. % | | | | | | | | | |
| Benzene | 43 | 42 | 42 | 43 | 42 | 43 | 43 | 42 | 42 |
| Xylenes | 57 | 57 | 56 | 57 | 57 | 56 | 57 | 57 | 57 |

In order to more fully illustrate the nature of the present invention and the manner of practicing same, the following examples are presented.

EXAMPLE 1

MCM-49 was prepared as in Example 6 of U.S. Pat. No. 5,236,575 (Ser. No. 07/802,938), incorporated herein by reference. It was converted to hydrogen form by nitrogen calcination at 538° C. for three hours followed by an aqueous ammonium nitrate exchange and de-ionized water wash. After drying at about 120° C. the activation procedure was completed by a three hour 538° C. calcination in air.

EXAMPLE 2

For comparison purposes, MCM-22 was prepared as in Example 1 of U.S. Pat. No. 4,954,325, incorporated herein by reference. It was converted to hydrogen form by nitrogen calcination at 538° C. for three hours followed by an aqueous ammonium nitrate exchange and de-ionized water wash. After drying at about 120° C. the activation procedure was completed by a three hour 538° C. calcination in air.

The H+ MCM-22 was found to contain 500 ppm sodium, so the ammonium exchange/air calcination cycle was repeated on a portion of the H+ MCM-22.

EXAMPLE 3

An atmospheric pressure, glass unit equipped with an on-line gas chromatograph was utilized for the disproportionation studies. Feedstock reactants were delivered to the unit through a syringe pump, and the catalyst bed temperature was monitored by a thermopcouple placed in the reactor's radially centered thermowell.

Samples of MCM-22 (once exchanged and twice exchanged) from Example 2 and MCM-49 from Example 1 were sized to 14/40 mesh. A 0.2 gram sample of sized zeolite was charged to the glass reactor and the unit heated to 260° C. at atmospheric pressure in a stream of 10 cc/min of $N_2$. After one hour at 260° C., toluene was introduced to the unit at a rate of 1.00 g/hr (5 WHSV). The $H_2$/hydrocarbon mole ratio was 0. Thirty minutes after the introduction of toluene an on-line gas chromatograph sample was taken to analyze for toluene conversion and selectivity to benzene and mixed xylenes. Fresh catalyst samples were loaded and the experimental procedure repeated at reactor temperatures of 315° C. and 371° C. A comparison of results is presented in Table III.

At 371° C. toluene conversion over MCM-49 was about 20% higher, with equivalent benzene and xylenes selectivities, than observed over MCM-22. At lower temperatures the toluene disproportionation levels for the two materials were comparable. Conversion appears by this data to reach a threshold for MCM-22 catalyst, while increasing further with MCM-49 catalyst, all the while maintaining selectivity.

What is claimed is:

1. A process for converting feedstock comprising an alkylaromatic compound, the alkyl group of said alkylaromatic compound having from 1 to about 6 carbon atoms, to conversion product which comprises contacting said feedstock comprising said alkylaromatic compound under disproportionation conditions with catalyst comprising an active form of synthetic porous crystalline MCM-49.

2. The process of claim 1 wherein the synthetic porous crystalline MCM-49 has a composition comprising the molar relationship

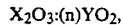

$$X_2O_3:(n)YO_2,$$

wherein n is less than about 35, X is a trivalent element and Y is a tetravalent element.

3. The process of claim 2 wherein n is from about 2 to less than about 35.

4. The process of claim 3 wherein n is from about 10 to less than about 35.

5. The process of claim 2 wherein X is a trivalent element selected from the group consisting of aluminum, boron, iron, gallium, and mixtures thereof, and Y is a tetravalent element selected from the group consisting of silicon, titanium, germanium, and mixtures thereof.

6. The process of claim 5 wherein X comprises aluminum and Y comprises silicon.

7. The process of claim 1 wherein said synthetic porous crystalline MCM-49 has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

8. The process of claim 1 wherein said synthetic porous crystalline MCM-49 has been thermally treated at a temperature up to about 925° C. in the presence or absence of steam.

9. The process of claim 7 wherein said synthetic porous crystalline MCM-49 has been thermally treated at a temperature up to about 925° C. in the presence or absence of steam.

10. The process of claim 1 wherein said catalyst comprises a matrix material.

11. The process of claim 10 wherein said matrix material is selected from the group consisting of alumina, silica, zirconia, titania, and mixtures thereof.

12. The process of claim 1 wherein said feedstock comprises toluene.

13. The process of claim 1 wherein said feedstock comprises an alkylnaphthalene.

14. The process of claim 13 wherein said alkylnaphthalene is methylnaphthalene.

15. The process of claim 1 wherein said feedstock comprises one or a mixture of compounds selected from the group consisting of toluene, methylnaphthalene, cumene, ethylbenzene, butylbenzene, ethylnaphthalene, isopropylnaphthalene and methylbiphenyl.

16. The process of claim 1 wherein said feedstock comprises toluene and $C_9+$ aromatic compounds.

17. The process of claim 1 wherein said disproportionation conditions include a temperature of from about 175° C. to about 675° C., a pressure of from about atmospheric to about 2,000 psig, a weight hourly space velocity of from about 0.1 $hr^{-1}$ to about 500 $hr^{-1}$ and a hydrogen/hydrocarbon mole ratio of from 0 to about 10.

18. The process of claim 12 wherein said disproportionation conditions include a temperature of from about 250° C. to about 595° C., a pressure of from about atmospheric to about 1,000 psig, a weight hourly space velocity of from about 0.1 $hr^{-1}$ to about 30 $hr^{-1}$ and a hydrogen/hydrocarbon mole ratio of from 0 to about 10.

19. The process of claim 13 wherein said disproportionation conditions include a temperature of from about 250° C. to about 675° C., a pressure of from about atmospheric to about 3,000 psig, a weight hourly space velocity of from about 0.1 $hr^{-1}$ to about 500 $hr^{-1}$ and a hydrogen/hydrocarbon mole ratio of from 0 to about 10.

* * * * *